United States Patent [19]

Hughes

[11] Patent Number: 4,620,670

[45] Date of Patent: Nov. 4, 1986

[54] GAS-POWERED NEBULIZER

[75] Inventor: Nathaniel Hughes, Palm Springs, Calif.

[73] Assignee: Vortran Corporation, Culver City, Calif.

[21] Appl. No.: 652,753

[22] Filed: Sep. 18, 1984

Related U.S. Application Data

[63] Continuation-in-part of Ser. No. 555,703, Nov. 28, 1983.

[51] Int. Cl.$^4$ .................... A61M 11/06; B05B 7/26
[52] U.S. Cl. ...................... 239/338; 128/200.21; 239/370; 239/DIG. 20
[58] Field of Search ............ 239/102, 338, 370, 590, 239/590.3, 590.5, DIG. 20, DIG. 23; 128/200.18, 200.21, 726; 261/78 A, DIG. 65

[56] References Cited

U.S. PATENT DOCUMENTS

| | | | |
|---|---|---|---|
| 4,198,969 | 4/1980 | Virag | 239/338 |
| 4,241,877 | 12/1980 | Hughes | 239/590.3 |
| 4,253,468 | 3/1981 | Lehmbeck | 128/726 |
| 4,301,970 | 11/1981 | Craighero | 239/338 |
| 4,453,542 | 6/1984 | Hughes | 239/338 |

*Primary Examiner*—Joseph F. Peters, Jr.
*Assistant Examiner*—Michael J. Forman
*Attorney, Agent, or Firm*—Christie, Parker & Hale

[57] ABSTRACT

The nebulizing device (44') and apparatus (10) for supplying nebulized liquids or powders for inhalation is provided. The device (44') include a base (108) having a closed bore (50) and an annular passageway (60) extending from the bore to an outlet (62). At least one auxiliary passage (62) is provided which extends through the base from the bore and opens to the passageway. Compressed gas is supplied through a supply hose (52) to the bore. A liquid port (118) extends from a liquid supply to the passageway adjacent the outlet such than when compressed gas is supplied to the bore the gas flows through the passageway and is discharged from the outlet, generating a subatmospheric pressure region to draw the liquid through the port into the passageway, the gas further generating a vortex action to nebulize the liquid. A plurality of screens (88, 92, 100) may be provided in series to further slow and nebulize the liquid. The apparatus includes a container (12). A top (22) is affixed to the container and includes a cavity (40). Nebulized liquid passes, in series, through the screens which act in cooperation with the device (44, 44') to provide a nebulized liquid.

2 Claims, 7 Drawing Figures

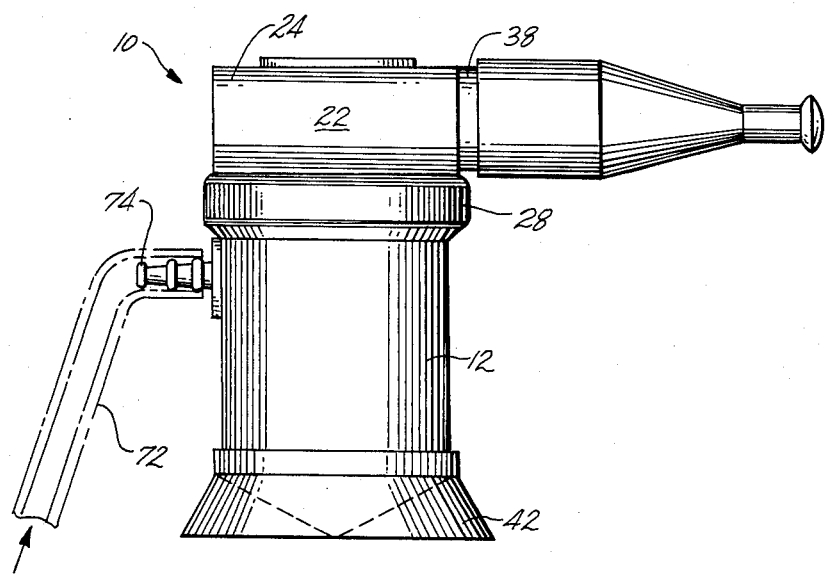
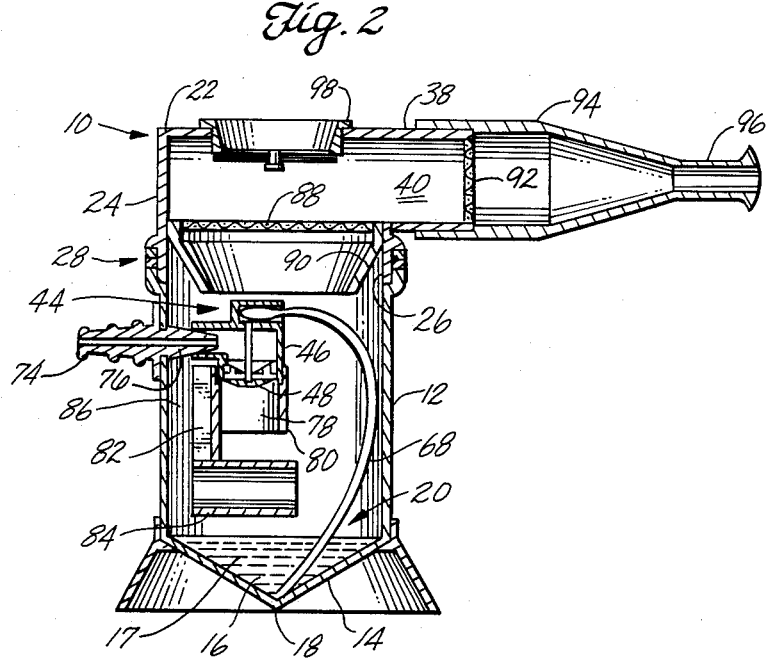

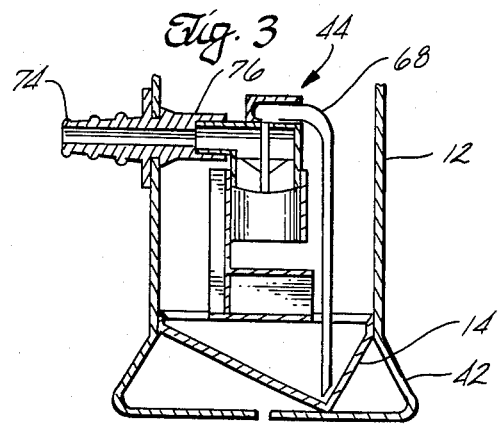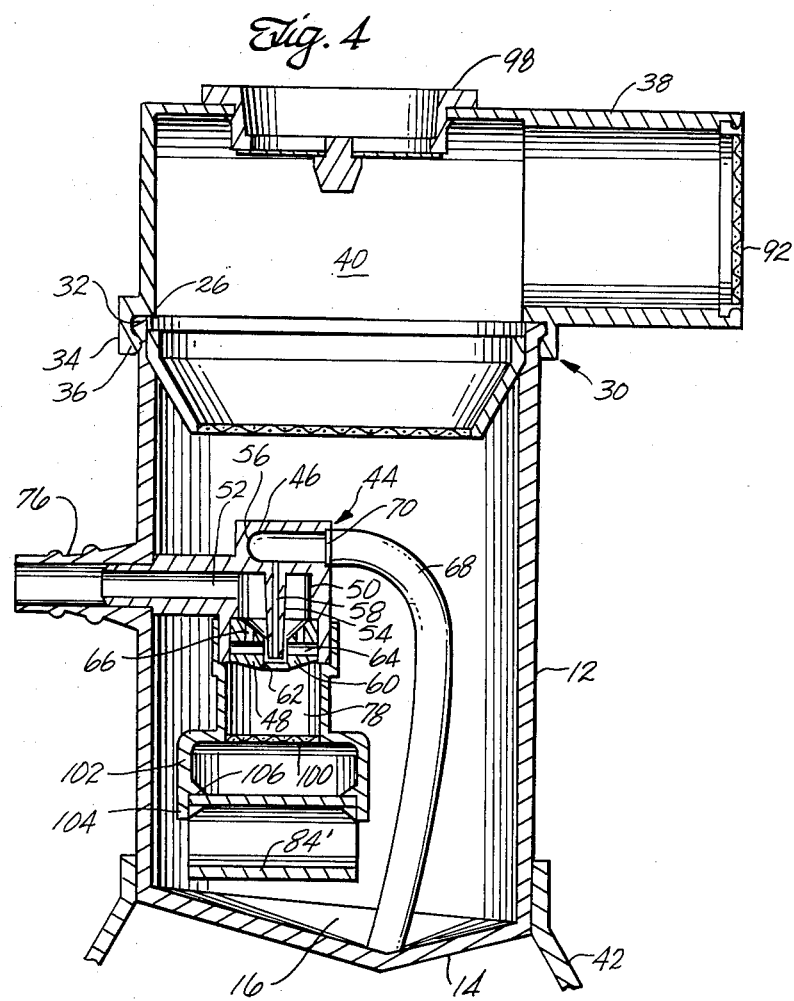

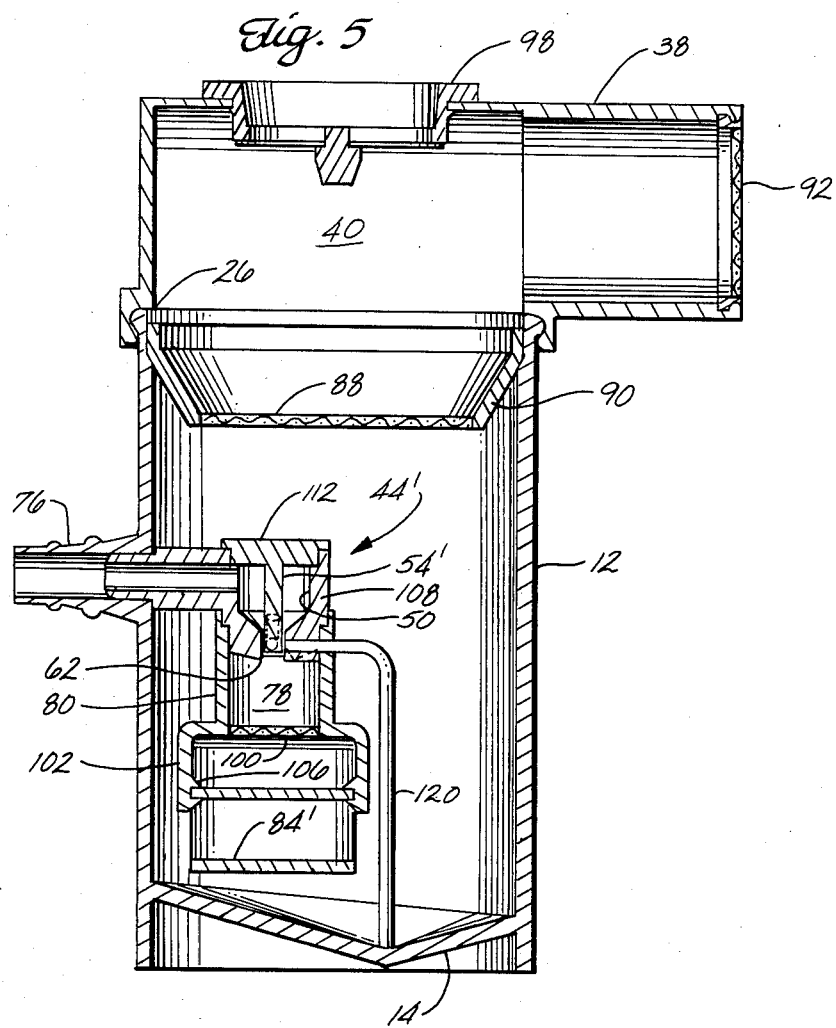

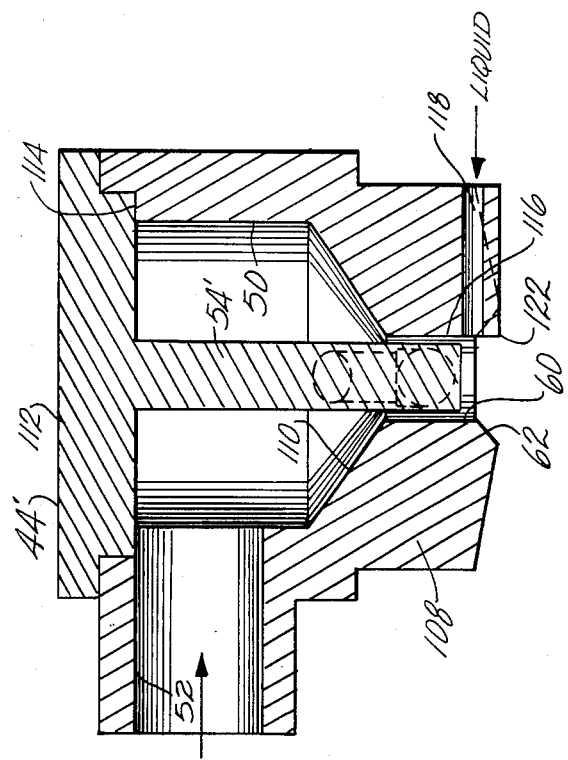
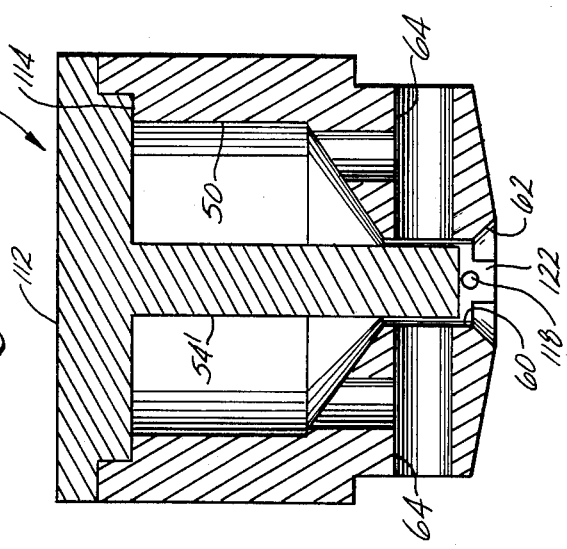

GAS-POWERED NEBULIZER

CROSS REFERENCE TO RELATED APPLICATION

This application is a Continuation-In-Part of U.S. application Ser. No. 555,703, filed Nov. 28, 1983 by Nathaniel Hughes and entitled "Atomizing Apparatus", the disclosure of which is hereby incorporated herein.

FIELD OF THE INVENTION

This invention relates to atomizers and more particularly atomizers for nebulizing liquid medicaments for inhalation.

BACKGROUND OF THE INVENTION

Atomizers, nebulizers and the like have been used to produce sprays, mists or fogs for a variety of uses, both in manufacturing and in-home use. According to one particular use, medicaments have been nebulized for inhalation. Medicaments as used herein shall be understood to include powdered or liquid drugs, solutions, vaccines, water and the like. In a usual fashion medicaments are often administered through injection or ingestion. For certain respiratory problems (i.e., asthma) it has been generally known to provide for the inhalation of aerosol medicaments. While injection and ingestion are quite popular in a hospital setting, for home use, particularly, injection can be troublesome. Associated with injection are hepatitis, vein collapse and overall discomfort to the patient.

It is believed that some, if not many, medicaments heretofore injected or ingested could be better and more conveniently administered by inhalation. Particularly for respiratory problems, direct inhalation of the medicament is highly preferred to injection or ingestion, which both require relatively large dosages to ensure that a desired amount of the medicament reaches the lungs or the desired effect takes place therein.

To provide for inhalation, various devices have been developed as exemplified by U.S. Pat. No. 4,453,542, issued June 12, 1984 to Hughes and entitled "Vortex Generating Medical Products". Other products have also been developed, particularly for nebulizing medicaments.

SUMMARY OF THE INVENTION

There is, therefore, provided in the practice of the present invention a device for nebulizing liquid and for supplying such nebulizing liquid for inhalation which is inexpensive and simple to manufacture and which is effective in producing a nebulized liquid useful for inhalation of medicaments.

Toward this end the device includes a base having a closed chamber and an annular passageway extending from the chamber to an outlet. At least one auxiliary passage is provided which extends through the body from the chamber and opens to the passageway. To drive the device, means are provided for supplying a compressed gas to the chamber. To supply liquid to the device a liquid conduit extends from a liquid supply to the passageway adjacent the outlet such that when compressed gas is supplied to the chamber, the gas flows through the passageway and is discharged from the outlet, generating a subatmospheric pressure region to draw the liquid from the supply through the conduit into the passageway, the gas further generating a vortex action to nebulize, i.e., atomize, the liquid.

Acting in concert with the device, a plurality of screens may be provided in series to further slow fluid flow and break up liquid droplets and generate further vortices for the efficient nebulization of the liquid.

To supply a liquid medicament to a patient, the nebulizing device is incorporated with an apparatus adapted to provide for such inhalation. The apparatus includes a container to retain an amount of liquid medicament, the ullage of the container defining a receiving chamber. A top is affixed to the container and includes a cavity which communicates at one end with the receiving chamber and terminates at its other end at an outlet port. Means, such as the nebulizing device discussed above, for nebulizing the liquid are provided arranged to discharge the nebulized liquid into the receiving chamber. To provide for the further nebulization of the liquid and slowing of the flow, a screen is disposed adjacent the cavity one end and another screen is disposed at the outlet port. Accordingly, the nebulized liquid discharged from the nebulizing means occupies the receiving chamber and thereafter passes, in series, through the screens which act in cooperation with the nebulizing means to provide a nebulized liquid at the outlet port for inhalation. This embodiment is also suitable to supply nebulized powders.

If desired, an inhalation mouthpiece may be provided at the outlet port, the mouthpiece being adapted to be received into the patient's mouth for inhalation. In conjunction with the mouthpiece, means such as a check valve or the like, may be included in the apparatus so that when the patient inhales at the mouthpiece the check valve admits ambient air (or breathing oxygen if the apparatus is incorporated into an oxygen supply) to augment the volume of nebulized medicament produced so that the patient may inhale a full breath. In addition, the air or oxygen admitted through the check valve tends to sweep the atomized medicament to the mouthpiece.

To atomize the medicament, means are provided to atomize the liquid medicament into droplets, each preferably of a diameter between 1–3 microns monodispersed. Droplets in this size range are indispensable to proper penetration and coating of the receptor sites in the bronchial tree to properly and fully medicate the patient.

BRIEF DESCRIPTION OF THE DRAWINGS

These and other features and advantages of the present invention will become appreciated as the same becomes better understood with reference to the specification, claims and drawings wherein:

FIG. 1 is a side view of an apparatus for the inhalation of nebulized medicament;

FIG. 2 is a side section view of the apparatus of FIG. 1;

FIG. 3 is a partial view of the apparatus similar to FIG. 1 showing a further embodiment of the container for the apparatus;

FIG. 4 is an enlarged side section view of a portion of the apparatus showing a further embodiment of the means for atomizing the medicament;

FIG. 5 is a view of the apparatus similar to that of FIG. 4 showing yet another embodiment of the means for atomizing the medicament;

FIG. 6 is an enlarged side section view of a device for nebulizing a liquid such as medicaments and the like; and FIG. 7 is a section view of the device of FIG. 6 rotated 90° from the view of FIG. 6.

DETAILED DESCRIPTION

Turning to FIGS. 1 and 2, an apparatus 10 is shown which is adapted for the inhalation of nebulized medicaments. The apparatus 10 includes a container 12 which may be fashioned from glass or plastic and which is open at one end and has a contoured bottom 14 at the other end. The contoured bottom defines a well 16 suitable for holding an amount of medicament 17, the well having a lowermost apex 18 so that substantially all the medicament may be nebulized as hereinafter set forth. The ullage above the medicament defines a receiving chamber 20 adapted to receive nebulized medicament.

The apparatus 10 also includes a top 22 having a cylindrical and hollow portion defining a trunk 24 with an open end 26 adapted to register with the receiving chamber 20. Opposite the open end 26 the trunk is closed.

To affix the top 22 to the container 12, suitable connection means are provided. For example, as shown in FIG. 2, a bayonette-type connection 28 may be provided or, as shown in FIG. 4, a suitable snap connection 30 may be employed. As shown, the snap connection 30 includes an outwardly extending lip 32 extending about the circumference of the open end of the container 12 while the top 22 includes a circumferential ring 34 having several or preferably a continuous, inwardly directed tab 36 adapted to snap over the lip 32, thereby connecting the top 22 to the container 12.

To provide a discharge for the nebulized medicament, the top 22 has, as shown in FIGS. 1, 2 and 4, a radially positioned, hollow outlet port 38. Accordingly, it can be appreciated that the top 22 includes a cavity 40 which extends from the open end 26 to the outlet port 38. As described below, the nebulized medicament passes from the receiving chamber 20 through the cavity 40 for inhalation thereof.

To provide a stand for the apparatus 10, a conical skirt 42, as shown in FIGS. 1 and 2, may be affixed to the container 12 adjacent the bottom 14. Alternatively, as shown in FIG. 3, the skirt 42 may be a continuation of the container 12 with the bottom 14, shown as bottom 14' in FIG. 3 being affixed by sonic welding or via an adhesive within the container 12.

To nebulize, i.e. atomize, the medicament, the apparatus 10 has incorporated therein nebulizing means shown in FIG. 2 as a nebulizer 44. The nebulizer 44 is adapted, along with the other components within the apparatus 10, to transform the liquid medicament into droplets of a size within the range of 1-3 microns monodispersed. This range of droplet size is believed to be the only way to efficiently disperse the medicament, when inhaled, throughout the lungs and to the alveolae thereof.

The nebulizer 44, as shown in FIG. 4, includes a chamber body 46 and an insert or base 48 which are preferably injection-molded parts. A chamber or large cylindrical bore 50 and a small cylindrical bore 52, which opens into bore 50, are formed in body 46. Bores 50 and 52 lie on intersecting orthogonal axes. Body 46 includes a hollow, cylindrical rod 54 that extends the length of bore 50 in axial alignment therewith. A small cylindrical bore 56 is formed in body 46 behind rod 54. Bores 52 and 56 lie on parallel axes. A bore 58 extends through rod 54 from bore 56 to the exterior end of bore 50.

Insert 48 fits into bore 50 where it is cemented or otherwise suitably affixed in place. A cylindrical aperture 60, which has a slightly larger diameter than rod 54, is formed in insert 48. Rod 54 extends through aperture 60 in axial alignment therewith to form therebetween a small annular passage. The open end of bore 58 is preferably recessed slightly from the exit end of aperture 60. The interior end of insert 48 has a conical concavity and the exterior end thereof has a spherical convexity. A conical concavity is formed between the center of convexity and aperture 60 defining a discharge 62 for the body 44.

Oppositely disposed radial bores 64 extend through insert 48 from its periphery to bore 78. A pair of oppositely disposed axial bores 66 extend through insert from its concavity to radial bores 64, thereby forming with bores 64 a pair of auxiliary passages. Liquid medicament is delivered by a conduit 68 and a coupling 70 to bore 56 which serves as the liquid inlet of the nebulizer 44. Bore 52 serves as a gas inlet to receive pressurized gas from a hose 72 (FIG. 1). The hose 72 extends from a source of pressurized gas (not shown) which may be air, oxygen, freon, liquified gas propellant or other gas suitable for inhalation.

To provide for the connection of the hose 72 to the apparatus 10, a fitting 74 is affixed to the container 12 as shown in FIGS. 1, 2 and 3. The fitting 74 includes an external portion which the hose 72 slips over for connection thereto. Within the container 12 the fitting has a finger 76 adapted to connect into the bore 52 or about the body (FIG. 3) and to support the nebulizer 44 within the chamber 20. Alternatively, as shown in FIGS. 4 and 5, the fitting 74 may be embodied as an external portion formed as part of the container 12 and adapted to connect the hose 72. In this instance, the body 46 includes an extension received into the external portion to support the nebulizer 44. Accordingly, pressurized gas supplied via the hose 72 is communicated by the fitting 74 to the bore 52 and to bore 50.

Bore 50 serves as an upstream section of a flow passage while aperture 60 serves as a restriction in the flow passage. Discharge 62 serves as the outlet of vortex generating nebulizer 44. Bores 50, aperture 60, and discharge 62 all are aligned with a flow axis. The gas inlet is aligned with an inlet axis that intersects the flow axis at a right angle.

The nebulizer 44, as shown in FIG. 2, further includes a spin chamber 78 embodied as a tubular member 80 having a cylindrical inner surface aligned with the flow axis of the nebulizer. At one end member 80 is connected to body 46. At the other end, the member 80 opens into the receiving chamber 20.

To enhance nebulization of the liquid, means are provided to slow the fluid discharged from the nebulizer 44. These means include a drag bar 82 and, in a one-piece construction, a bluff body or cylindrical drag member 84. Drag member 84 is connected by a support arm 86 to the tubular member 80 and is so mounted relative to the spin chamber 78 that the cylindrical axis of drag member 84 lies at a right angle to the flow axis of the gas through the spin chamber 78.

Briefly, pressurized gas from a source is introduced into the nebulizer through gas inlet bore 52. The gas forms rapidly spinning vortices in the upstream section of the flow passage. The vortically flowing gas travels through the restriction formed by aperture 60 and rod 54 and through the auxiliary passages so as to converge near the open end of rod 54 where the rapidly moving gas meets liquid supplied through rod 54. The gas thus entrains and nebulizes the liquid to form liquid particles in the gas on the order of about 1–10 microns. At the discharge 62 a subatmospheric pressure is produced that draws liquid through rod 54 and causes cavitation in this liquid as it emanates from the end of rod 54. Liquid nebulization is enhanced by a supersonic process taking place in the nebulizer. As a result, shock waves are formed as the gas exits aperture 60 and sonic energy in addition to vortex energy is present in spin chamber 78.

At very low flow velocities, i.e., Reynolds numbers, the drag coefficient, and thus the drag forces, increase rapidly. At such low Reynolds numbers, viscosity is a predominant parameter in determining drag and viscosity effects dominate over gravitational effects.

Drag member 84 presents drag to and induces vortex action in the gas and liquid stream and it sets up a standard sonic wave field to further break up the droplets as the fluid is discharged into and occupies the receiving chamber 20. From the receiving chamber 20 the nebulized medicament-gas mix (i.e., fluid) passes through the container open end, the passageway 40 and to the outlet port 38 for inhalation.

To further slow fluid velocity and drag to generate additional vortices and to break up droplets of medicament, the apparatus 10 includes a first screen 88 disposed near the connection between the top 22 and the container 12. As shown in FIG. 2, the first screen 88 may be disposed at the base of an inverted, frustro-conical collar 90 supported by the trunk 24. Alternatively, as shown in FIG. 4. the first screen 88 may be disposed at the frustrum of the collar 90. In the event that the apparatus 10 is tipped over, the collar will prevent loss of medicament. The collar 90 may be made of resilient material to provide a sealing function between the top 22 and container 12.

To still further slow the fluid flow, increase drag and break up droplets, the apparatus 10 includes a second screen 92 disposed at the outlet port 38. The nebulized medicament flowing from the receiving chamber through the first screen 88 and cavity 40 passes through the second screen 92 for inhalation thereof. At the discharge of the outlet port the effective size of the liquid droplets has been reduced such that most of the droplets have a diameter of 1–3 microns monodispersed. The flow of the nebulized medicament has also been slowed which is advantageous for inhalation. Each of the first and second screens may be made of wire or nylon mesh or a square grid fashioned such that the spacing between adjacent parallel strands is about 0.06 inch (1.524 mm).

To provide for the ease of inhalation, the apparatus 10 may include a mouthpiece 94 having a suitable bite 96 for reception into the patient's mouth. Accordingly, the nebulizer medicament may be drawn from the passageway 40 through the outlet port 38 and hollow mouthpiece 94 into the patient's lungs.

To augment the volume of gas/nebulized medicament produced by the nebulizer and present within the apparatus 10, means are provided for introducing a further source of gas such as air or oxygen. As shown in FIG. 2, these means may be embodied as a check valve 98 of the flapper type adapted to prevent release of nebulized medicament. However, upon inhalation at the mouthpiece 94, the check valve 98 will open permitting outside air to be drawn into the top 22 and, more particularly, the passageway 40 so that a full, deep breath may be drawn at the mouthpiece to distribute the medicament throughout the lungs. It is to be understood that an oxygen source, such as a hose, may be connected to the check valve 98 such that, upon inhalation, oxygen provides the additional volume necessary to constitute a deep breath.

Turning to FIG. 4, modifications are shown for enhancement of the nebulization of the medicament. According to this embodiment, a third screen 100 is disposed at the terminus of the tubular member 80 and between the discharge 62 and drag member 84. The third screen is adapted to slow the fluid leaving the discharge 62, generate vortices and resonate sound waves to break up droplets. Connected to the tubular member 80 are a pair of oppositely disposed arms 102, each having at its end a foot 104 including a notch 106. To cooperate with the arms 102, the drag member shown as 84' is embodied as a length of cylindrical conduit which may be snapped between and into the notches of the arms 102. By providing the arms 102, drag members 84' of differing diameters may be freely interchanged to achieve the desired drag and vortex producing effect based upon, for example, the viscosity of the medicament or other factors.

Turning to FIGS. 5–7, still another embodiment of the apparatus 10 and, more particularly, the nebulizer 40 incorporated therein will be described. Elements similar to those described above will carry the same reference numerals, whereas those modified elements will carry a prime (') designation.

The nebulizer 44 has a body 44' including a base portion 108 having fashioned therein the bore 50. The base portion 108 may be injection molded plastic or the like. The bore 50 terminates at one end at a conical concavity 110, itself terminating at the aperture 60. The cylindrical aperture 60 is arranged to be coaxial with the bore 50. The aperture 60 intersects the coaxially arranged, conically diverging discharge 62. The small cylindrical bore 52 is fashioned in the base portion 108 and, as described above, is adapted to admit pressurized gas into the bore 50. The pressurized gas spins within the bore 50 and is discharged therefrom via the aperture 60 and discharge 62.

To induce the vortex action, a cap 112 is affixed and mates with a countersink 114 fashioned in the base portion 108. The cap 112 is adapted to close and seal the bore 50. Extending axially from the cap 12 is a solid cylindrical rod 54' which passes axially through the bore 50 into the aperture 60 to terminate just short of the discharge 62. The annular space about the rod 54' within the aperture 60 defines an annular passageway 116 which acts as a restriction to induce and enhance the vortex action.

Oppositely directed radial bores 64 extend through the base portion 108 from its periphery to aperture 60. A pair of oppositely disposed axial bores 66 extend through the base portion 108 from concavity 110 to the radial bores 64, thereby forming with bores 64 a pair of auxiliary passages. Accordingly, the pressurized gas flows through these auxilary passages to the aperture 60.

To introduce the liquid medicament to the nebulizer 44', the base portion 108' includes a liquid port 118 extending through the insert to terminate at the intersection between the aperture 60 and the discharge 62.

From the liquid port 118 a small tube 120 extends downwardly to the well 16 to draw liquid medicament upward to the nebulizer 44'. Unlike the embodiment described above, the introduction of liquid does not require elaborate molding or manufacturing methods necessary to fashion the hollow rod 54 or the bore 56. According to this embodiment, the liquid port 118 can simply be drilled or otherwise fashioned (i.e., laser drill) through the insert 48' to terminate at the aperture and discharge. In order to accommodate the liquid port, the insert 48' is fashioned to have at the conical discharge 62 a built-up portion 122 so that the liquid port 118 discharges radially into the aperture 60 and discharge 62.

It is to be understood that the device and its various embodiments described above are suitable for nebulizing other liquids such as paint or others where a fine spray is desirable. Additionally, by placing finely ground powders (medicaments or others) in the container, these powders may also be delivered. For delivery of powders the liquid port 118 or bore 56 are blocked and the bluff body 84, 84' may be removed. The vortex and shock wave action generated by the nebulizer lifts and vibrates the powder for delivery from the device to, if the powder is a medicament, the patient's lungs.

While I have shown and described certain embodiments of the present invention, it is to be understood that it is subject to many modifications and changes without departing from the spirit and scope of the appended claims.

What is claimed is:

1. A device for nebulizing liquid with a compressed gas comprising:
    a chamber body including a chamber base portion, a chamber bore, a discharge and a restrictive annular passageway extending from the chamber bore to the discharge and an auxiliary passage passing through the chamber base portion from the chamber bore to the passageway;
    a closure for the chamber bore;
    means for supplying the compressed gas to the chamber bore;
    a liquid port to admit liquid through the chamber base portion to the discharge to supply liquid thereto, the compressed gas flowing through the passageway and to the discharge and mixing with the liquid to nebulize the liquid;
    a tubular member comprising a first end adjoining the discharge and a second end opposite the first end and a screen disposed at the second end of the tubular member; and
    a bluff body spaced from the screen to slow flow of nebulized liquid and generate vortices wherein the bluff body comprises first and second ends and is supported at the first and second ends, respectively, by first and second arms which are supported by the tubular member and wherein the arms are spreadable for interchangeably receiving bluff bodies of different sizes.

2. A nebulizer for supplying a nebulized medicament comprising:
    a container to retain an amount of medicament and comprising an ullage, the ullage defining a receiving chamber;
    a top connected to the container and including a cavity communicating at one end with the receiving chamber and terminating at the other end at an outlet port;
    means for generating nebulized medicament into the receiving chamber;
    a first screen disposed adjacent the cavity one end to slow the flow of nebulized medicament from the receiving chamber to the cavity and enhance nebulization, wherein the first screen is supported by a truncated conical collar having a reduced diameter portion projecting into the receiving chamber, the collar preventing spillage of the medicament; and
    a second screen disposed at the outlet port to further slow the flow of nebulized medicament as it is discharged from the outlet port and enhance nebulization.

* * * * *